United States Patent [19]
Wyatt et al.

[11] Patent Number: 5,656,490
[45] Date of Patent: Aug. 12, 1997

[54] ENZYME COMPOSITIONS AND METHODS FOR BIODEGRADATION SEPARATION OF NATURAL FIBERS AND ADSORBED PETROLEUM PRODUCTS

[76] Inventors: Caryl Heintz Wyatt; Bobby Gene Wyatt, both of 3410 37th St., Lubbock, Tex. 79413; Deborah L. Carr, 5806 78th St., Lubbock, Tex. 79424

[21] Appl. No.: 444,960

[22] Filed: May 19, 1995

Related U.S. Application Data

[63] Continuation-in-part of Ser. No. 96,615, Jul. 23, 1993, abandoned.

[51] Int. Cl.$^6$ .................................................. C07G 17/00
[52] U.S. Cl. .................. 435/281; 435/262; 435/262.5; 435/263; 435/264; 435/267; 510/320; 8/401
[58] Field of Search ................................. 435/262, 262.5, 435/263, 264, 267, 281; 252/174.12; 8/401

[56] References Cited

U.S. PATENT DOCUMENTS 3,843,517  10/1974  McKinney et al. ..................... 435/281
5,120,463  6/1992  Bjork et al. ............................ 435/264

*Primary Examiner*—Helen Pratt
*Attorney, Agent, or Firm*—Harris, Tucker & Hardin, P.C.

[57] ABSTRACT

A method is presented for releasing petroleum and hydrocarbon products sorbed onto or entrained by organic natural fibers in an aqueous medium through the use of enzymes to degrade the organic natural fiber sorbents utilized for oil spill cleanup, the method provides an opportunity for achieving responsible separation of oil from oil spill sorbent materials. Natural organic fibers which have been utilized to adsorb petroleum and hydrocarbon products are separated from these petroleum and hydrocarbon products by reducing the natural organic fiber links to the point that the adsorbed or entrained oil no longer has sufficient binding surface or fiber link to remain held by the fibers, thus floats to the surface of the aqueous medium. Aqueous medium enzyme compositions are provided which are suitable for degrading organic natural fibers inclusive of cellulose-based and protein-based fibers resulting in release of adsorbed, absorbed and/or entrained petroleum products.

39 Claims, No Drawings

ENZYME COMPOSITIONS AND METHODS FOR BIODEGRADATION SEPARATION OF NATURAL FIBERS AND ADSORBED PETROLEUM PRODUCTS

CROSS-REFERENCE TO RELATED APPLICATION

This application is a continuation-in-part of U.S. patent application Ser. No. 08/096,615, filed Jul. 23, 1993 now abandoned.

FIELD OF THE INVENTION

The present invention relates to aqueous medium enzyme compositions suitable for degrading natural fibers inclusive of cellulose-based and protein-based fibers and separating them from adsorbed, absorbed and/or entrained petroleum products. In another aspect the invention relates to a method of utilizing the aqueous medium enzyme compositions for removing adsorbed petroleum products, crude oil and other non-aqueous liquids from natural fibers which have adsorbent capabilities for these materials through biodegradation of the natural fibers. In still another aspect, the invention relates to a method for removing petroleum and hydrocarbon materials from the surface of water utilizing natural fibers as adsorbents and separating the petroleum products from the natural fibers through enzyme degradation of the fibers in an aqueous medium.

Petroleum and hydrocarbon product spills produce an immediate and very observable impact on ecosystems. This impact can be minimized by appropriate rapid responses, ranging from controlled burning of, for example oil spills, to in situ bioremediation. Physical sorbents represent a direct approach to removal of spilled oil. These physical adsorbents can represent the primary removal method in the case of small spills, or adsorbents may serve to supplement mechanical equipment such as skimmers in the case of larger spills. Presently used physical adsorbents are not without problems regarding their usage, primarily the problem of reuse and/or disposal of petroleum or hydrocarbon product-soaked adsorbents.

Various chemicals have been used such as detergents and surface active agents to disperse oil spills. In most cases they only spread the spills over a larger area or allow them to sink into the water. Also, these chemicals are frequently pollutants which kill marine life. In most cases the chemicals are expensive and the oil cannot be salvaged for processing. Several oil adsorbing materials have been used such as straw or vermiculite to spread on the surface of the contaminated water where the oil leakage or spillage occurs. Saw dust is another particulate used in such oil spills on water, highways, drilling figs, manufacturing areas and on the ground along beaches and coastal locations. These items have good adsorption advantages. However, when these materials are removed they ultimately become waste products and oil cannot be recovered.

Disposal of oil soaked adsorbents is frequently accomplished by placement in approved landfills, but this procedure is rather expensive and an economically undesirable approach. Approved incineration vastly reduces the amount of residual material associated with the disposal of used adsorbents, but such a process is also very expensive and may result in air pollution problems. Ideally, adsorbents would be reused on site and some adsorbents are fabricated or planned for reuse. Worn, reusable adsorbents must be properly disposed of and in the urgent context of spill clean-up, single use adsorbents are frequently more convenient. A recycling procedure has been suggested for a widely used adsorbent, airblown polypropylene fibers. These pads would be returned to the manufacturer for solvent extraction of hydrocarbons from the pads, then the airblown polypropylene fiber for example would be refabricated. In other procedures, for example non-woven fiber webs constructed of very short fibers of waste cotton, i.e. linters, ginmotes and mill wastes, are utilized in providing recovery of spilled oil products; however, separation of the recovered off products from the mat is by mechanical squeezing. U.S. Pat. No. 4,832,852 discloses use of a non-woven fiber mat for removing oil from a surface contaminated with the oil followed by separation of the oil from the mat by mechanical squeezing. U.S. Pat. No. 5,156,743 discloses a method for removing oil from the surface of a body of water using a layered sheet comprised of natural fibers to adsorb oil between the layers and the sheet, with the sheet later being removed from the water surface and compressed to squeeze oil from between the layers of the sheet.

Natural fibers are biodegradable and also possess a strong adsorbency for petroleum and hydrocarbon products and therefore should be considered for use as adsorbents at oil spill sites. Peat moss, raw dust, paper and paper waste products as well as cellulose fibers such as cotton and protein-based fibers such as wool and like are frequently used for this purpose. These natural fibrous materials may contain amounts of lignin or other compounds which are resistant to rapid biodegradation. Cotton fibers are essentially free of lignin and can be biodegraded. In contrast to processed cotton, raw cotton has considerable potential for selective removal of spilled off and hydrocarbon products from surface waters, since the natural waxes on the raw cotton make it preferentially oil wet. This potential was recognized by Robert F. Johnson, et al. in an article entitled "Removal of Oil from Water Surfaces by Adsorption on Unstructured Fibers", *Environmental Science & Technology*, 7:439–443, 1973. However, biodegradation of natural fibers is generally undesirable. U.S. Pat. No. 5,120,463 specifically proportion cellulase multi-enzyme systems which are directed to detergent compositions useful as laundry detergents wherein said compositions possess excellent cleansing abilities while exhibiting reduced degradation potential against cotton fabrics.

The enzymatic modification of raw materials has been an important component of industrial processes for decades. However only recently has an increased understanding of molecular structure and function enabled workers to design processes which can utilize the enormous capability provided by naturally evolved catalytic systems, known as enzymes. Industrial applications are by no means equally distributed over the various classes of enzymes. Emphasis has been strongly biased toward hydrolytic enzymes, and more specifically toward peptide hydrolysis (the proteases). This biased leaning is a result of important industrial processes based on the action of intrinsic or exogenous hydrolytic activities. The bating (hair removal) of hides and leather production using the endogenous proteases and the natural saccharification of starch by amylases in alcoholic fermentations are two obvious examples. Also, the production of high fructose syrups by enzymatic action is a major industry.

Successfully creating industrial uses of enzymes is a more difficult task than it might appear. Two approaches require the identification of a process where existing enzymes might be utilized and improved or the finding of interesting or new enzymes followed by searching for a suitable advocation, both of these approaches require considerable experimentation and discovery.

Industrial use of enzymes presents multiple problems including costs, limited range of use regarding temperature, pH and the like as well as low solubility in aqueous solutions. However, enzymes can offer high or low specificity and can be selected to suit the desired biological function. Use of enzymes produce little or no by product formation and optimum activity occurs under very mild reaction conditions.

Enzyme specificity which can be a great advantage is also a disadvantage in the requirement for experimentation and discovery to determine specific enzyme combinations for specific biochemical outcomes. One enzyme, or perhaps one enzyme complex, catalyzes each biochemical reaction. Different enzymes possess specificities and it is possible to select an enzyme for a given process. Specificity not only reduces interference by undesirable substrates but minimizes the problems of unwanted byproducts.

The term "cellulase" refers to a multi-enzyme system which acts on crystalline and amorphous forms of cellulose and its derivatives to hydrolyze cellulose and gives primary products, oligosaccharides, glucose and cellobiose. Cellulases are known in the art to be useful in detergent compositions, either for the purpose of enhancing the cleanability of the compositions or as a softening agents. Also, cellulases are used in fabric finishing operations where a soft feel or hand is desirable on the material. Cellulases in this application remove a portion of the fibers perpendicular to the surface of the cloth and produce a smoother fabric. However, regardless of its cleaning and/or softening mechanism, the use of cellulases in detergent compositions is complicated by the factor that exposure of cotton garments to cellulase results in partial degradation of the cotton fabric in these garments. Cellulases are known in the art as enzymes that hydrolyze cellulose (beta-1-4-glucan linkages) thereby resulting in the formation of glucose, cellobiose, and the like.

In view of the prior art efforts in using sorbents to soak up petroleum and hydrocarbon product spills, selectivity of the materials utilized and use and reuse of said materials, it is readily understood that such modern methods fail to address the total need of the environment as welt as efficiency requirements when non-biodegradable sorbents are used to help clean up oil spilled on large water surfaces. Present systems utilize synthetic as well as natural fibers to adsorb the petroleum and hydrocarbon product materials from the surface of water or other sources. However, the separation of the petroleum and hydrocarbon materials from the synthetic and/or natural fibers is generally achieved by squeezing, thus leaving a residual petroleum/hydrocarbon content in the fibers which either must be burned or presented to a landfill. None of these prior systems suggest the use of enzymes for the release of petroleum hydrocarbons from natural fiber adsorbents used for off spills. Accordingly, it would be highly desirable to provide an improved, ecologically sound method which utilizes simple and commonly available inexpensive natural fibers which do not require manufacturing of fabrics, sophisticated process equipment or utilize other chemicals which can become contaminants to the environment as well.

Accordingly, it is an objective of this invention to develop enzymatic methods for the biodegradation of natural fiber sorbents and contaminant release of entrained or adsorbed petroleum/hydrocarbon materials for separation from the fibers. It is a further object of the invention to provide a method of removing oil from the surface of water utilizing sorbents that can be degraded in aqueous medium enzyme compositions. These and other objects are achieved by the present invention as evidenced by the attached summary of the invention and detailed description of the invention and claims.

SUMMARY OF THE INVENTION

The present invention is directed to the discovery that use of enzyme compositions are suitable for releasing petroleum and hydrocarbon products sorbed on to or entrained by organic natural fibers in an aqueous medium. The use of enzymes to degrade the organic natural fibers sorbents used for aquatic oil spill clean-up provides a unique opportunity for achieving responsible separation of oil from oil spill adsorbent materials. Degradation in a reaction chamber of fibrous mats by enzymes contained in an aqueous medium releases the oil adsorbed to, or entrained in, the organic natural fibers by reducing fiber lengths to the point that the adsorbed oil no longer has sufficient binding surface or fiber length to remain held by the fibers and thus floats to the aqueous medium surface. The oil or hydrocarbon product can then be recovered from the aqueous medium surface including sea water, using appropriate skimming and other methods. Efficiency separation rates by volume of 95–99% can be achieved as tested with diesel or light crude oils. The fibers undergo further degradation if allowed to remain in contact with the enzyme solution. Degradation of, for example, 90% by weight of cotton and cellulosic fibers has been obtained using cellulase as the enzyme. Residual material in this instance is comprised of cellulose, glucose and other non-degradable components of cotton. In addition, natural protein-based products such as wool and collagen or gelatin pads utilized as adsorbents for petroleum and hydrocarbon products can be separated from these contaminants in aqueous media utilizing proteases as the enzyme. However the process when degrading wool is enhanced through utilization of a reducing agent in order to break the disulfide cross linkages of wool.

In its method aspects, the present invention is directed to a method for removing oil from the surface of water using sorbents and a method of removing oil from natural fiber adsorbents containing petroleum and hydrocarbon products through the utilization of various enzymes in an aqueous medium.

DETAILED DESCRIPTION OF THE INVENTION

Fiber has been defined as a relatively long, continuous piece of material made up of fine filaments. A fiber actually refers to a structure rather than a specific substance with the possibility of many substances combining to form the complicated matrix that we call fiber. The matrix can be comprised, for example of microfibrils of cellulose, a rigid glucose polymer. Hemicelluloses, pectins and other gums surround the cellulose as binding materials and in addition this matrix can be impregnated with lignin which can be visualized as a matrix in which the fibers are embedded. From this discussion of fibers, it is apparent that a single enzyme is not capable of totally hydrolyzing all the components of many natural fibers. In addition, the presence of many other components may hinder enzymes from reaching their substrate in the matrix. Frequently pretreatment methodologies such as grinding have been found necessary in order to achieve extensive hydrolysis of fiber components before effective enzyme treatment can be accomplished.

Therefore, industry interest in the production and use of cellulolytic enzymes has been slow in developing probably because of the complexity of the cellulolytic enzyme system and the resistance of cellulose to rapid and efficient hydrolysis by enzymes and because of lack of cost-effectiveness.

Cellulose, one of many natural fibers, is probably the most abundant biological compound on earth and is found either in pure form (cotton) or in the form of lignified cellulose (wood) and can be found in more refined purity states such as in paper, fibers and textiles. Cellulose is the predominant waste material in agriculture in the form of stalks, stems, husks, gin trash and the like. Cellulose is one of the main waste products, both in nature and man-made materials. Cellulose is a linear glucose polymer coupled by $\beta(14)$ bonds. Starch is a glucose polymer linked by $\alpha(1-4)$ bonds. Cellulose polymers can be very long and the number of glucose units in the cellulose molecule can vary from 15 to 15,000 with a mean value of about 3,000. Cellulose strands are usually coupled together by hydrogen bonds to give larger units. There remain different opinions about the number of cellulose molecules in such units and how they are organized. However it is thought that one area of the molecule will have regions of orderly configuration, rigid and inflexible in structure such as in crystalline cellulose and other regions of string-like flexibility in structure such as amorphous cellulose.

Cellulose fibers adsorb water and swell. The swelling is limited to the amorphous regions of the fiber. Strong hydrogen bonding network of the crystalline regions prohibit swelling. The number of bonds available for enzyme action will depend upon the degree of swelling of the cellulose, thus for sufficient hydrolysis of cellulose by cellulases, pretreatment to promote swelling is frequently necessary. Or in the alternative, reactions within an aqueous medium would promote such swelling and enhance enzymatic hydrolysis of the cellulose molecules. Cellulases are enzymes that degrade cellulose and are comprised of several different enzymes which are required to break down cellulose to glucose. In the breakdown of cellulose before pure glucose or relatively pure glucose is achieved, the fibers are reduced in length and size by degradation. These enzymes can attack cellulose through two modes. Endocellulases are capable of hydrolyzing the $\beta(1-4)$ bonds randomly along the cellulose chain and exocellulases cleave off glucose and/or cellobiose molecules from one end of the cellulose strand. These two modes of attack are also observed for amylases and proteases on their respective substrates. Enzyme preparations containing only endocellulases have little effect on native cellulose. On the other hand, those containing both endo- and exocellulases will cause significant degradation of cellulose. Thus the endo- and exocellulases work in a systematic and cooperative and/or synergistic manner on cellulose.

The hydrolysis product of simultaneous endo- and exocellulases activities are glucose, oligosaccharides and cellobiose, a disaccharide. As the cellobiose concentration increases in the reaction mix, exocellulase activity is inhibited. To obtain extensive cellulose hydrolysis, a procedure for removing cellobiose is needed. The enzyme cellobiase will achieve this by cleaving the cellobiose into two glucose molecules.

Cellulases, commercially available, generally include mixtures of the following enzymes.

Systematic Name: 1,4-$\beta$-D-Glucan glucanohydrolase Endocellulase

Reaction Catalyzed: It randomly hydrolyzes $\beta(1-4)$ bonds in cellulose yielding oligosaccharides Source: *Trichoderma reesei, T. viride, Aspergillus niger*

Systematic Name: 1,4-$\beta$-D-Glucan glucohydrolase Exocellulase

Reaction Catalyzed: It hydrolyzes $\beta(1-4)$ bonds in $\beta$-glucans so as to remove successive glucose units, Hydrolyzes cellobiose slowly Source: *Trichoderma reesei*

Systematic Name: 1,4-$\beta$-D-Glucan cellobiohydrolase Exocellobiohydrolase

Reaction Catalyzed: It hydrolyzes $\beta(1-4)$ bonds in cellulose to release cellobiose from the nonreducing ends of the chains Source: *Trichoderma reesei, T. viride*

Systematic Name: $\beta$-D-Glucoside glucohydrolase Cellobiase

Reaction Catalyzed: It hydrolyzes the $\beta(1-4)$ bond in cellobiose, giving two molecules of glucose Source: *Aspergillus niger, T. viride, & cerevisae*

Cellulase is defined as a system of enzymes that hydrolyzed cellulose ($\beta$-1,4 glucan linkages) resulting in the formation of oligosaccharides of varying lengths, cellobiose and glucose. Several different enzyme components (Methods in Enzymology, 160, 25, pp. 234 et seq., 1988) or classes of enzymes comprise the cellulase system. This includes:

(a) endoglucanases (b) exoglucanases (c) exocellobiohydrolase (d) cellobiase (=$\beta$-glucosidase)

These enzymes appear to work in a synergistic or cooperative manner to degrade cellulose. Each class may be composed of one or more component enzymes and the ratios of these components in the cellulase system may vary. Commercial cellulase preparations may deliberately be enriched for one or more components for accomplishing a particular purpose.

Another natural fiber, wool, that has neither been injured mechanically nor modified chemically is more resistant to attack by proteolytic enzymes such as pepsin, trypsin, chymotrypsin; however, papain and protease type IV were found to be effective. When the cuticle or scale layer of the fibers is damaged by mechanical means, the wool becomes much more susceptible to attack by pepsin and chymotrypsin. Under these conditions only a small portion of the wool is digested, yet the fibers are considerably weakened and their fiber structure is partially destroyed.

Most natural fibers, i.e. formed by natural means in nature versus fibers made from natural materials, can be categorized as proteins from animals such as wool; or cellulose from plants, such as cotton. When processed for use in textiles, these natural fibers become relatively easily wet by water, if they have been treated to remove surface oils and waxes; hence they are not highly suitable for selective adsorption of oil from an aquatic oil spill. Natural fibers must repel water to prevent water from soaking into the fiber and causing subsequent damage to the animal or plant. To fulfill this need, wool is coated with significant amounts of water repellent materials generally called lanolin. Similarly, unprocessed cotton fibers are coated with wax, which is a high molecular weight ester.

Cotton and wool with their surface waxes and oils still present appear to be natural fibers of choice for use as oil sorbents since the infrastructure for their large-scale growth, collection and marketing already exists. A typical price for apparel-grade wool is $1.30 per pound. An American Wool Council spokesperson estimated that 14 million pounds of wool which is unsuitable for apparel are available each year.

This wool, whose fibers are too coarse and/or too short for apparel has a lessor value. Some of this poor quality wool is the result of raising lambs for meat, and keeping ewes for lamb production. Two forms of wool adsorbents were shown at the recent International Oil Spill Conference in Tampa. Wool adsorbent pads of weights varying from 6 to 12 ounces per yard were shown by Western Textile Products, and knopps, approximately ½ inch aggregates of wool developed in New Zealand were represented in the United States by Joymai Environmental.

A considerable amount of BG, below grade cotton, is produced as a result of early frosts and other adverse growing conditions. The amount produced in Texas alone varies from 2 to 85 million pounds per year. The potential for using cotton as an oil adsorbent was recognized in the late 70's at Texas Tech University, but the impetus for its actual use did not come until the recent increase in environmental awareness. At least one firm is producing cotton pads and booms for aquatic oil spills. Other natural fibers have been tested for use as oil spill sorbents, but these materials are not readily available at a low cost. These materials include milkweed, kenaf and kapok fibers.

Oil spill sorbents based on recycled newsprint, wood byproducts, and other plant materials are also available. For use with aquatic oil spills these materials may need to be made water repellent by special chemical treatments. These woody adsorbents generally contain significant amounts of lignin. Lignin degrades rather slowly, usually by fungi, hence the relative permanence of wood. For this reason, these lignin containing materials would be expected to biodegrade less rapidly and/or less completely than adsorbents made from relatively pure cellulose such as cotton, or protein such as wool.

Table 1 indicates the physical properties of a number of biodegradable adsorbents and polypropylene adsorbents. For purposes of this disclosure, the term adsorbed shall include absorbed and/or entrained. As would be expected all effective adsorbents have very large porosities, above 90%, so that a large quantity of oil can be retained relative to the weight of adsorbent used. The fiber diameters were uniform for cotton and wool due to their biological origin, whereas the diameters of the polypropylene fibers varied widely due to the method of manufacture. The air permeability and resulting calculated specific surface areas indicate that the polypropylene fibers are on the average finer than the natural fibers.

The oil-adsorbent capabilities, measured by the ASTM F726 procedure, are similar for all products tested except for raw cotton, whose capacity was considerably higher. These tests were made on a sweet West Texas Crude, whose initial API gravity was 33.3. Prior to testing the crude was weathered by blowing air through the crude oil until 30 weight percent of the crude had been vaporized. The resulting weathered crude oil had an API gravity of 23.8 and a viscosity of 73 cp. The oil capacities for two typical adsorbents using this crude oil at various stages of weathering indicate little change in adsorption capacity as a function of weathered viscosity. Cotton and wool perform effectively relative to polypropylene adsorbents.

In general, it can be observed that the natural fiber pads show similar performance capabilities to the polypropylene pads. It has been shown that unprocessed cotton is an effective adsorbent relative to polypropylene materials. Tests have shown the natural fiber pads including wool and cotton to be more effective than polypropylene pads. An oil capacity of 21.6 grams of heavy crude per gram of sorbent was reported for a 12 ounce wool pad compared to 12 to 17 grams heavy crude/gram of polypropylene adsorbent.

It should be stressed that these results are comparing commercial polypropylene pads, which presumably have been optimized for performance, with experimental cotton and wool pads whose adsorbent capacities have not yet been optimized. These results do clearly demonstrate that biodegradable pads made of either cotton or wool can perform effectively as adsorbents in comparison to commercial polypropylene products.

Disposal of oil-soaked natural fiber adsorbents using biological methods is possible because both the oil and the adsorbent are naturally occurring materials, and eventually will undergo biodegradation. Tasks in "developing" ex situ biologically based methods for the disposal of this material included finding ways to do it faster than the rate at which it would occur naturally in the environment, and developing a means for doing it under conditions where the material was confined and would not be released into any environmental sink. In addition, since two different materials had to be degraded, fiber and oil, another task was to determine whether degradation should be done sequentially, i.e. first degrade one, then degrade the other, or simultaneously.

In the interest of being able to better control and understand each process, it was decided that the best way to proceed would be to first find a way to degrade each substrate by itself, then to determine if each one could be degraded in the presence of the other. What is described below are some of the procedures we used to develop the technology for disposing of natural fiber sorbents with entrained hydrocarbons.

Adsorbents made of natural fibers (cotton or wool) are naturally biodegradable. They are broken down by microbial and/or enzymatic activity within a time frame of several weeks in a closed environment where optimum conditions for degradation can be provided and controlled. The structural integrity of the sorbents was degraded first releasing their entrained oil. This allowed the oil to be separated and recovered from the residual sorbent and the medium in which degradation occurred, for example, aqueous medium. Residues to be disposed of from this process include undegraded sorbent (generally 15% or less of the original amount) consisting of extremely short fibers which collectively form a "fluff" of material which has no collective structural integrity and the medium in which the adsorbent degradation occurred. As long as these residues do not contain hazardous levels of hydrocarbons, such residues can be disposed of as non-hazardous waste. The oil released from the adsorbent can be either recovered or degraded biologically. Recovery methods include those standard in the industry for separating petroleum hydrocarbons from aqueous media.

Table 1 presents various natural and man-made fibers frequently used as adsorbents.

TABLE 1

Adsorbents

| Product | Shape and Thickness | Specification | Porosity | Permeability ($cm^2$) × $10^6$ | Fiber length (cm) | Fiber diameter (μm) | Specific surface area** ($cm^{-1}$) |
|---|---|---|---|---|---|---|---|
| Texas raw cotton | loose fiber, NM* | cellulose fiber | 0.99 | NM | 1.63 | 14 | NM |
| Cotton Pad | needle-punched sheet, ½" | cellulose fiber | 0.98 | 6.90 | 1.70 | 16 | 165 |
| Wool Pad | needle-punched sheet, ¼" | wool fiber | 0.95 | 8.43 | 2.69 | 24 | 143 |
| 3M HP156 polypropylene | sheet, ¼" | melt-blown fiber | 0.96 | 2.26 | NM | 0.5–36 | 280 |
| ERGON E100 | sheet, ⅜" | melt-blown fiber | 0.93 | 3.27 | NM | 3–10 | 222 |
| SPC 100 polypropylene | sheet, ⅜" | melt-blown fiber | 0.94 | 2.14 | NM | 0.85–9.4 | 279 |

*NM - not measurable
**calculated from Kozeny-Carman Equation:
$K = cP^3/S^2$ where K is permeability, P porosity, S specific surface area, c = 0.2

Wool fibers in which the disulfide cross-linkages have been broken, as by mechanical reduction, are almost completely digested by pepsin and chymotrypsin but are attacked only slightly by trypsin. Table 2 presents enzyme by type, supplier and degradation utilization suitable in accordance with the invention.

TABLE 2

| Enzyme | Type | Vendor | Substrate |
|---|---|---|---|
| Rapidase ® | Cellulase | International Bio-Synthetics | Cellulose (raw cotton) |
| Indiage ® | Cellulase | Genecor | Cellulose (raw cotton) |
| Cellusoft ® | Cellulase | Novo Nordisk | Cellulose (raw cotton) |
| Protease: Type IV | Protease | Sigma Chem. Co. | Wool (raw, unscoured) |
| Papain | Protease | Spectrum Chemical Manufacturing Corp. | Wool (raw, unscoured) |
| Protease: Type IV | Protease | Sigma Chem. Co. | Collagen (formed pad) |

CELLULASES AND THEIR MANUFACTURERS

Enzyme: Rapidase®GL
Manufacturer: GIST-BROCADES, formerly INTERNATIONAL BIO-SYNTHETICS
P.O. Box 241068
Charlotte, N.C. 28224-1068
(704) 527-9000
CAS Name: Cellulase
GAS Number: 9012-54-8
Product Code: 5299
Producing Organism: *Trichoderma reesei*
Activity: measured in carboxymethyl cellulase units* (CCUs)=98-106 CCU/gram liquid
Enzyme dosage recommended: 0.5–2.0%, O.W.G. (on weight of goods)
Note: Both CCU and CMC are abbreviations for carboxymethyl cellulase units.
(Units are International Units (IU) 1 IU liberates 1 μmole reducing sugar (expressed as glucose equivalents) in 1 minute under standard conditions (50 C at pH 4.8)

Enzyme: IndiAge™ 44L
Manufacturer: Genencor International
4 Cambridge Place
1870 South Winton Road
Rochester, N.Y. 14618
(716) 256-5200
CAS Name: Cellulase
GAS Number: 9012-54-8
Product Code: CL601
Producing Organism: *Trichoderma reesei*
Activity: 2500 CMC units/ml*
Enzyme dosage recommended: For treating denim: a) 5–10 ml enzyme/kg denim if treated for 20–30 minutes, or b) 2.5–5 ml if treated for 30–45 minutes.

Enzyme: Denimax L
Manufacturer: Novo Nordisk Bioindustrials, Inc.
33 Turner Road
P.O. Box 1907
Danbury, Conn. 06813-1907
(203) 790-2600
Chemtrec Number: (800) 424-9300
GAS Name: Cellulase
GAS Number: 9012-54-8
Producing Organism: *Trichoderma humicola isoenls*
Activity: measured in endoglucanase units (EGUs)=90 EGU/gram
Enzyme dosage recommended: 2% enzyme, 50°–60° C., pH 6–8.

Enzyme: Cellusoft L
Manufacturer: Novo Nordisk Bioindustrials, Inc.
33 Turner Road
P.O. Box 1907
Danbury, Conn. 06813-1907
(203) 790-2600
Chemtrec Number: (800) 424-9300
CAS Name: Cellulase
GAS Number: 9012-54-8
Producing Organism: *Trichoderma reesei*
Activity: 750 EGU/gram
Enzyme dosage recommended: 0.5 to 2.0% on fabric weight

PROTEASES AND THEIR MANUFACTURERS

Enzyme: Protease, Type IV: Bacterial, purified
Manufacturer: Sigma Chemical Company
P.O. Box 14508

St. Louis, Mo. 63178-9916
Producing Organism: *Streptomyces caespitosus*
Activity: 0.7–1.0 unit per mg solid*
Enzyme: Protease, Type V
Manufacturer: Sigma Chemical Company
P.O. Box 14508
St. Louis, Mo. 63178-9916
Producing Organism: *Streptomyces griseus*
Activity: 0.7–1.0 unit per mg solid*
Note: This item was discontinued by the manufacturer in 1980. It is the same enzyme as Type XIV, differing from it in that Type V contained a starch extender.
Enzyme: Protease, Type VI (Pronase P)
Manufacturer: Sigma Chemical Company
P.O. Box 14508
St. Louis, Mo. 63178-9916
Producing Organism: *Streptomyces griseus*
Activity: 3–4 units per mg solid*
Note: This item was discontinued by the manufacturer in 1980. It is the same enzyme as Type XIV, except it was referred to as a Pronase P (P grade) rather than as Pronase E.
Enzyme: Protease, Type XIV, Bacterial, (Pronase E)
Manufacturer: Sigma Chemical Company
P.O. Box 14508
St. Louis, Mo. 63178-9916
Producing Organism: *Streptomyces griseus*
Activity: approximately 4 units per mg solid*
*Protease, unit definition:
One unit will hydrolyze casein to produce color equivalent to 1.0 μmole (181 μg) of tyrosine per minute at pH 7.5 at 37° C. (color by Folin-Ciocalteu reagent), unless otherwise indicated.

Cotton is a filament of cellulose ready for use by the textile industry at a minimal price. It has been proposed recently to use cotton as a sorbent for oil spills. Due to cotton's physical properties, it accumulates oil readily and it is also a natural, biodegradable, non-polluting fiber. The present invention answers how to degrade the cotton in the easiest, quickest, and most complete manner possible using biological methods. Since attempting to degrade the oil soaked cotton as a whole is a difficult and complicated task, it is easier to try to degrade the oil and the cotton separately in order to have a general idea of what must be done to degrade the two as a whole and to determine which is the more effective way to do this. Thus an object of the invention was to determine the optimum conditions for degradation of cotton using enzymes in order to achieve quick and high efficiency release of sorbed oil.

Cellulase enzymes have been used for practical purposes in food processing and in the denim garment industry. They are used in the latter to improve the "hand" (or soft feel) of denim. Cellulase, in part, or entirely, replaces the "stone-washing" process. The tiny cotton fibers which stick up from the cloth when it is new are digested by the cellulase (or abraded away by the stones), thus making the fabric feel smooth. Once the cellulose molecules which comprise the surface fibers have been partially hydrolyzed, mechanical action then can remove the weakened surface fibers.

When cotton is treated with cellulase, there is a weight reduction and a loss in strength proportional to the amount of weight reduction. When the enzyme is first applied to the cotton, it begins to react with the cellulose fiber, partially hydrolyzing the molecules of cellulose. This occurs because the cellulase breaks the β-1, 4-glycosidic bonds of the cellulose molecule. Breaking the bonds by the hydrolytic chemical reaction catalyzed by cellulase removes glucose and cellobiose units from the cellulose molecule, making it smaller.

Cellulase enzymes generally are characterized by the pH range in which they are most effective. These categories include: acid stable, neutral stable, and alkaline stable. Cellulase degradation of cotton and oil soaked rags and papers generally used acid stable enzymes which perform best between pH values of about 3.5 to about 6.5.

In addition to pH, temperature is another critical factor which must be controlled. The temperature must be high enough for optimum enzyme activity, but low enough so that the enzyme does not denature. In order to optimize the cotton degradation, a proper ratio of time, temperature, pH, and amount of cellulase are required. Each of these parameters was tested experimentally to determine the optimum conditions for degrading the cellulose. Although most acid stable cellulase enzymes are most effective at temperatures of about 20° C. to about 60° C., a pH range of about 3.5 to about 6.5, and at concentrations of between about 50 to 100 ml enzyme solution per liter as supplied by the manufacturer, the amount degraded may vary depending on the enzyme source. Supplies of enzyme solutions provide technical procedures utilizing for example, cellulase, "On Weight of Good (O.W.G.)" bases, volume of prepared enzyme solution to weight of good (cotton) treated. According to the present invention, OWG of enzyme solution to natural fibers ranged from about 4 to about 30% (O.W.G.). Effective amounts of enzyme solution usage will vary depending on the natural fiber and/or specific enzymes. Thus, it was necessary to determine experimentally how each of these parameters affected the ability of various cellulase enzymes to degrade cotton. The goal was to degrade the maximum amount of cotton in the minimum amount of time.

Several commercial adsorbents including adsorbent pads made from wool and cotton, plus raw cotton have been tested for adsorption capacity, adsorption rate, and oil selectively. The tests generally followed the ASTM F726 procedure. In this procedure for adsorption capacity and adsorption rate, adsorbents are placed on the surface of oil contained in a shallow tray until visibly saturated and then drained for 30 seconds and weighed.

In the oil selectivity procedure, an absorbent pad, about 100×120 mm in size, is placed into a horizontal, 1-gallon jar, half full of water, and mechanically shaken at 150 cycles per minute for 30 minutes. Oil is added in 25 ml increments and shaken for an additional 30 minutes. The oil addition procedure is repeated until a layer of free oil remains on the water surface after shaking for 30 minutes, which implies saturation of the pad with oil. After draining for 2 minutes, the pad is weighed. The adsorbed liquid is extracted from pad with hexane, and water is separated from the hydrocarbons in a separatory funnel. The amount of oil adsorbed in the presence of water is obtained from total weight, dry pads weights and water weight.

The first series of tests employed 20 weight non-detergent motor oil as the test fluid. In general, the raw cotton showed significantly superior performance in all categories. It had approximately twice the adsorption capacity of next best material, Titan polyurethane pad, 60 versus 29 g oil/g adsorbent. The adsorption rate for raw cotton was only slightly higher than for other materials. In the presence of water; in the low rate oil exposure test, raw cotton was 50% better the next best material, a polypropylene pad, 3M-HP-156, 29 versus 20 g oil/g adsorbent. The raw cotton did not sink during the low rate oil exposure tests.

The Cotton Unlimited cotton pad containing polyester fibers did not perform as well as the raw cotton in these same tests. The performance was rather similar to the polypropylene pads. The Cotton Unlimited pad increased in volume and lost its shape, as the result of shaking and exposure to water during the low rate oil adsorption test. The wool pad performed similarly to the synthetics, except that it showed a higher rate of adsorption. It did not sink, and retained its integrity during the low rate oil adsorption test.

A similar series of tests have been performed using diesel fuel as the oil. The results are very similar to those results observed in the previous tests with 20 weight motor oil. Due to the viscosity difference, adsorption rates are much higher for diesel than for motor oil, and, in the presence of water, oil adsorption capacities for diesel are lower than for motor oil, since fluids are allowed to drain from the pad for 2 minutes prior to weighing. Most significant change is for raw cotton, which has an adsorption capacity for diesel that is only one-half of that for motor oil.

The following examples are offered to illustrate the present invention as well as comparative examples outside the invention. The comparative examples are offered in order to illustrate the refinements necessary in selecting variables such as pH, temperature, time, enzymes and the like to meet the requirements of the invention, i.e. the use of enzyme compositions in aqueous medium for the biodegradation of natural fibers which have been utilized for adsorbing petroleum product and hydrocarbon product spills. The first series of examples, Examples 1–9 are concerned with the degradation of cotton by Rapidase® cellulase without oil being adsorbed on the cotton. These examples illustrate the impact of varying pH, temperature and the like. Examples 10–11 present similar studies utilizing cotton having oils adsorbed thereon. Examples 12–15 are presented for showing the impact of utilizing a seawater aqueous medium on the process. Examples 16–18 presents studies reusing the enzyme both with and without oil. Examples 19–22 present studies for the degradation of cotton utilizing Indiage® cellulase with variations in specific parameters. Examples 23–27 present enzyme degradation of, for example, wool and cotton utilizing enzymes other than with Rapidase® or Indiage®. Example 28 shows the effect of agitation speed on degradation by Rapidase®.

Experiments with Rapidase® (No Oils)

0.5 gram samples of raw cotton which had been dried and weighed to ±0.1 mg were placed in individual Erlenmeyer flasks with 75 ml of distilled water, the pH of which had been adjusted as indicated with either HCl or NaOH. The enzyme in the indicated activity units was added and incubation on a shaker at 200 rpm was carried out for the length of time indicated. The cotton residue then was recovered, dried and weighed to calculate percentage fiber digested.

EXAMPLE 1

Rapidase® (1 ml/75 ml medium) 102 CCU room temperature (RT) incubation, ca. 21°–22° C. 48 hr. incubation period
Purpose:
To test the ability of the commercial enzyme, Rapidase®, to degrade raw cotton and a commercially-available cotton pad (Cotton Unlimited, Post, Tex.).

Results:

| | % Cotton Degraded | | |
|---|---|---|---|
| | + Cellulase | − Cellulase | |
| Raw cotton | 14 | 3 | (both static and weathered) |
| CU pad | 16 | 3 | " |

Conclusions:
(1) More cotton was degraded in the presence of the Rapidase® enzyme than in its absence (true for both static and weathered [shaken] controls).
(2) There was no statistical difference in the amount degraded between the raw cotton and the Cotton Unlimited pad.

EXAMPLE 2

Rapidase® (various concentrations)
32° C.
pH4.0
days incubation period
Purpose:
To determine the optimum concentration of enzyme for maximum cotton degradation.

Results:

| Enzyme Concentration (mls & %) | % Cotton Degraded |
|---|---|
| 1 ml (1.33%) 102 CCU | 30 |
| 4 ml (5.06) 408 CCU | 40 |
| 8 ml (9.64) 816 CCU | 45 |
| 12 ml (13.79) 1224 CCU | 43 (repeat = 41) |
| Static control | 3 |
| Shaken control | 0.5 |

Conclusions:
(1) Maximum degradation was obtained with 4 ml enzyme (approximately 5%).
(2) Increasing the amount of enzyme above 4 ml did not increase the amount of degradation under these conditions.

EXAMPLE 3

Same set up as Example 2.
Purpose:
To repeat Example 2 but extend the incubation period to 6 days Results:

| Enzyme Concentration (mls & %) | % Cotton Degraded |
|---|---|
| 1 ml (1.33%) 102 CCU | 38 |
| 4 ml (5.06) 408 CCU | 63 |
| 8 ml (9.64) 816 CCU | 62 |
| 12 ml (13.79) 1224 CCU | 59 |
| Static control | 1 |
| Shaken control | 2 |

Conclusions:
(1) Maximum degradation occurred at 4 and 8% concentration of enzyme.
(2) Extending the incubation period to six days from three increased degradation at all concentrations of enzyme (but not in the controls which lacked enzyme).

EXAMPLE 4

Rapidase® (8 ml/75 ml medium) 816 CCU
32° C. incubation temperature 200 rpm
vary pH
3 day incubation
Purpose:
To determine the effect of pH, and optimum pH, on cotton degradation.

Results:

| pH | % Cotton Degraded |
|---|---|
| 3.5 | 56 |
| 4.0 | 58 |
| 4.5 | 63 |
| 5.0 | 58 |
| 6.0 | 42 |
| 7.0 | 26 |

Conclusions:

(1) Maximum degradation under these conditions occurred at pH 4.5.

(2) Good degradation between pH 3.5 and 5.0; less at pH 6.0 and poor at 7.0.

EXAMPLE 5

Same as Example 4 except:

(a) incubation extended to 6 days (b) a "minus enzyme" control was done at each pH tested.

Purpose:
To determine the effect of pH, and optimum pH, on cotton degradation to determine if low pH by itself leads to cotton degradation.

Results:

| pH | +/− enzyme | % Cotton Degraded |
|---|---|---|
| 3.5 | + | 53 |
| | − | 2 |
| 4.0 | + | 56 |
| | − | 1 |
| 4.5 | + | 66 |
| | − | 1 |
| 5.0 | + | 65 |
| | − | 1 |
| 6.0 | + | 47 |
| | − | 2 |
| 7.0 | + | 24 |
| | − | 2 |

Conclusions:

(1) Maximum degradation under these conditions occurred at pH 4.5 and 5.0.

(2) Good degradation between pH 3.5 and 5.0; less at pH 6.0 and poor at 7.0.

(3) No degradation in "minus enzyme" controls at each pH, thus pH alone does not affect degradation in the range tested.

For Example 6 and all remaining examples, the distilled water was replaced with McIlvaine buffer at pH 4.5 unless otherwise noted in the examples.

EXAMPLE 6

Rapidase® (8 ml) 816 CCU
pH 4.5 (buffered)
200 rpm
6 day incubation period

Purpose:
To determine the effect of temperature on cotton degradation.

Results:

| Temp °C. | +/− enzyme | % Cotton Degraded |
|---|---|---|
| 21–22 | + | 44 |
| | − | 0 |
| 40 | + | 77 |
| | − | 2 |
| 50 | + | 65 |
| | − | 0 |
| 55 | + | 63 |
| | − | 2 |
| 65 | + | 0 |
| | − | 4 |

Conclusions:

(1) Maximum degradation under these conditions occurred at 40° C.

(2) Good degradation also at 50° and 55°; but enzyme inactive at 65° C.

(3) No degradation in "minus enzyme" controls at each temperature, thus temperature alone does not affect degradation.

EXAMPLE 7

Rapidase® (4 ml) 408 CCU
pH 4.5 (buffered)
40° C. incubation temperature
200 rpm
vary incubation period: 3, 6, 9, 12 and 15 days Purpose:
To determine the effect of time on cotton degradation.

Results:

| Incubation Time (days) | % Cotton Degraded |
|---|---|
| 3 + enzyme | 50 |
| 6 + | 67 |
| 9 + | 76 |
| 12 + | 80 |
| 15 + | 90 |
| 15 − enzyme | 3 |

Conclusions:

(1) Maximum degradation (90%) under these conditions occurred in 15 days.

(2) The longer the incubation period, the more cotton degraded.

(3) No degradation in "minus enzyme" control at the longest incubation time.

EXAMPLE 8

Rapidase® (4 ml) 408 CCU
pH 4.5 (buffered)
40° C. incubation temperature
Either the medium was heated to 40° C. before adding the enzyme or it was not.
Incubation was either static or shaking.
Observations at 1, 2, 4, 6, 8, 24 and 48 hours after incubation beings.
Results will be measured by loss of integrity of cotton mat (dissolution into fluffy bottom layer on flask or not)

Purpose:

To determine:

(a) whether heating the solution to 40° C. before adding the enzyme hastens degradation.

(b) if agitation is needed for degradation or whether it will occur in static flasks.

(c) combination of (a) and (b).

Results:

(a) Static incubation: no degradation in 24 hr, and it did not make a difference whether the solution was heated before adding the enzyme or not.

(b) Shaking incubation:+degradation of mat in 24 hr, and it did not make a difference whether the solution was heated before adding the enzyme or not.

Conclusions:

(1) Heating the medium before adding the enzyme has no effect on cotton degradation (static or shaking incubation).

(2) Static incubation=no degradation, Shaking incubation=+complete degradation, as measured by loss of integrity of mat of cotton.

EXAMPLE 9

Rapidase® (4 ml) 408 CCU pH 4.5 (buffered)

40° C. incubation temperature 200 rpm 3 or 6 days incubation

Purpose:

To determine if there is a difference in the amount of substrate degraded between raw cotton and the Cotton Unlimited pad.

Results:

| Substrate | Days incubation | % Cotton Degraded |
|---|---|---|
| raw cotton | 3 | 48 |
| " | 6 | 66 |
| CU pad | 3 | 41 |
| " | 6 | 59 |

Conclusions:

(1) Raw cotton and CU pad were degraded about the same amount after 3 days of incubation; after 6 days of incubation.

(2) More degradation occurred after 6 days as compared to 3 days.

Rapidase® Experiments (with Oils)

For Examples 10 and 11, the 0.5 gram sample of dried and weighed cotton was allowed to soak up either crude oil or diesel fuel until saturated. The remainder of the procedure was the same as that previously described using McIlvaine buffer.

EXAMPLE 10

Rapidase® (4 ml) 408 CCU pH 4.5

40° C.

200 rpm

Purpose:

To determine if cotton can be degraded by the enzyme in the presence of diesel and crude oil (separately).

Results:

| Oil | Days | +/− enzyme | % Cotton Degraded |
|---|---|---|---|
| crude | 3 | + | 28 |
| diesel | 3 | + | 38 |
| none | 3 | + | 46 |
| crude | 6 | + | 64 |
| diesel | 6 | + | 65 |
| none | 6 | + | 60 |
| crude | 6 | − | 0 |
| diesel | 6 | − | 0 |

Conclusions:

(1) Cotton is degraded in the presence of either diesel or crude oil, and the oil is released and floats to the top of the flask.

(2) In the absence of the enzyme, cotton is not degraded and neither oil is released.

EXAMPLE 11

Rapidase® (4 ml) 408 CCU

40° C.

pH 4.5

200 rpm 5 ml diesel/0.5 g cotton or 5 ml crude oil/0.5 g time (hrs) varied: 3, 6, 24, 72

Purpose:

To determine how quickly oil is released from the cotton in the enzyme solution.

Results:

| Time (hrs) | Oil | Results |
|---|---|---|
| 3 | crude | no degradation, no oil recovered |
|  | diesel | no degradation, no oil recovered |
| 6 | crude | no degradation, no oil recovered |
|  | diesel | no degradation, 0.1 ml diesel recovered |
| 24 & 72 | crude | degraded, oil recovered |
|  | diesel | degraded, oil recovered |

Conclusions:

(1) Degradation of the cotton by the enzyme sufficient to release the oils occurred between 6 and 24 hr.

Rapidase® Experiments with Seawater

For Examples 12–15, Instant Ocean® sea salts were added to the experimental flasks in the concentrations indicated to determine the effect of simulated seawater on the enzymatic degradation of cotton, either in the presence or absence of crude oil or diesel fuel.

EXAMPLE 12

Rapidase® (4 ml) 408 CCU

40° C.

pH 4.5

200 rpm

±Instant Ocean salts added to the medium to simulate seawater (9 g/L, pH adjusted to 4.5 with HCl)

Incubation for 3 or 6 days

Purpose:

To determine if the enzymatic degradation of cotton is affected by the presence of the amount and kinds of salts normally found in seawater.

Results:

| Addition | Time (days) | % Cotton Degraded |
|---|---|---|
| Control (+ enzyme) | 3 | 48 |
| (McIlvaine buffer) | 6 | 69 |
| Control (no enzyme) | 3 | 0 |
| Instant Ocean | 6 | 0 |
| Experimental | 3 | 48 |
| (+ enzyme, | 6 | 68 |
| + Instant Ocean) | | |

Conclusions:

(1) Cotton degradation by enzyme was unaffected by the presence of seawater after either 3 or 6 days of incubation.

(2) No enzyme=no degradation.

EXAMPLE 13

Same as Example 12 except that either 5 ml of diesel or crude oil was added to the cotton; no (−) enzyme controls were run.

Purpose:

To determine if the enzymatic degradation of oil-soaked cotton is affected by the presence of the amount and kinds of salts normally found in seawater.

Results:

(a) no enzyme=no degradation or oil release (b) other results varied with individual flasks and times; some released both diesel and crude after three days while others did not; same for 6 days.

(c) pH was adjusted with HCl; when checked at the end of the experiment in the flash which had not released the oil; the pH was 5.3 to 6.0.

EXAMPLE 14

Same as Example 13 except McIlvaine buffered Instant Ocean was used.

Results:

| Medium | Time (days) | % Cotton Degraded | ml Oil Recovered |
|---|---|---|---|
| Instant Ocean | 3 | 0 | 0 |
| (diesel) | 6 | 51 | 3.7 |
| Instant Ocean | 3 | 46* | 3.9 |
| (crude oil) | 6 | 49** | 3.5 |
| Control (no enzyme, | | | |
| + diesel | 6 | 0 | 0 |
| + crude) | 6 | 0 | 0 |

*only two of three underwent complete degradation and oil release (results based on these two flasks)
**only one of three underwent complete degradation and oil release (results based on only this one flask)

Conclusions:

(1) Rapidase® released oil (diesel or crude) from cotton in seawater.

(2) Release was delayed (up to 6 days or more, vs. 24 hr.)

EXAMPLE 15

Rapidase® (4 ml) 408 CCU
40° C.
pH 4.5
200 rpm

Instant Ocean salts added to the medium to simulate seawater at concentrations ranging from 0.01% to 1%.

No oil added. Diesel oil added; or crude oil added
Incubation 6 days

Purpose:

To determine at what percentage of realistically occurring sea salts*, the release of hydrocarbons from and degradation of cotton is inhibited.

*"realistically occurring sea salts" means the concentration by weight which would be expected to occur in a pad which had been used to pick up oil from the ocean.

Results:

| % Seawater | Oil | % Degradation |
|---|---|---|
| 1% | none | 73 |
| 1% | diesel | 76 |
| 1% | crude | 75 |
| 0.5% | none | 74 |
| 0.5% | diesel | 74 |
| 0.5% | crude | 76 |
| 0.1% | none | 73 |
| 0.1% | diesel | 74 |
| 0.1% | crude | 74 |
| 0.01% | none | 75 |
| 0.01% | diesel | 72 |
| 0.01% | crude | 73 |
| 0% | none | 74 |
| 0% | diesel | 73 |
| 0% | crude | 73 |

Conclusion:

There was release of oil and cotton degradation within 6 days for all the concentrations of sea salts tested.

Rapidase® Experiments (Re-use of the Enzymes)

For Examples 16–18, the enzyme solution tested consisted of recovered enzyme solution used in previous examples; this was done to determine whether enzyme solutions could be reused, as described in each example.

EXAMPLE 16

Rapidase® (4 ml) 408 CCU
40° C.
pH 4.5
200 rpm
Incubation for 3 days

Purpose:

To determine if the enzymatic degradation of cotton (no added oil) can be accomplished by previously used enzyme solutions (not exposed to oils). Also, how does recovering the enzyme by filtration or centrifugation affect its activity as measured by the amount of cotton which remains at the end of the experiment (compared to new enzyme solution?)

Results:

| Medium | % Cotton Degraded |
|---|---|
| Filtered enzyme | 34 |
| Centrifuged enzyme | 40 |
| New enzyme (not used previously) | 46 |

Conclusions:

(1) Enzyme solutions previously used to degrade cotton are still active in degrading cotton alone (no oil added).

2) Approximately 10% loss in activity vs. new enzyme solution.

(3) Centrifuged enzyme had more activity than filtered.

EXAMPLE 17

Rapidase® (4 ml) 408 CCU
40° C.

pH 4.5

200 rpm

Incubation for 3 days

Purpose:

To determine if the enzymatic degradation of cotton (no added oil) can be accomplished by previously used enzyme solutions which had been exposed to oil (diesel or erode)

Results:

| Medium | Oil Exposure | % Cotton Degraded | % Activity Loss |
|---|---|---|---|
| Filtered enzyme | Diesel | 38 | 24 |
|  | Crude | 43 | 14 |
| New enzyme (not previously used) | None | 50 |  |

Conclusions:

(1) Enzyme solutions previously used to degrade oil-soaked cotton is still active in degrading cotton alone (no oil added).

(2) Some activity loss compared to new enzyme solution.

EXAMPLE 18

Rapidase® (4 ml) 408 CCU

40° C.

pH 4.5

200 rpm

Incubation for 3 days

New medium vs. medium recovered from Example 16 by either filtration or centrifugation Purpose:

To determine if the enzymatic degradation of cotton (no added oil) can be accomplished by enzyme solutions previously used twice (not exposed to oils).

Results:

| Medium | % Cotton Degraded | % Loss of Activity |
|---|---|---|
| Filtered enzyme | 34 | 26 |
| Centrifuged | 40 | 14 |
| New enzyme (not used previously) | 46 |  |

Conclusions:

(1) Enzyme solutions previously used to degrade cotton are still active in degrading cotton alone (no oil added).

(2) Some loss in activity vs. new enzyme solution.

(3) Some difference in enzyme activity with regard to the method for collecting the used enzyme solution (filtered lost more than centrifuged).

Experiments with Indiage®

The experimental protocol for Examples 19–22 was the same as that described for the previous examples, with Rapidase® being replaced with Indiage®, another commercially-available cellulase.

EXAMPLE 19

Indiage® (1, 4 or 8 ml/75 ml media) 2500, 10000 or 20000 CMC units pH 5.0 (Mfg. recommended)

50° C. incubation (Mfg. recommendation, 50°–55° C.)

3 day incubation period

Purpose:

To test the ability of the commercial enzyme, Indiage®, to degrade raw cotton. Various concentrations of enzyme were tested.

Results:

| Enzyme Concentration (mls & %) | % Cotton Degraded |
|---|---|
| 1 ml (1.33%) 2500 CMC units | 38 |
| 4 ml (5.06) 10000 CMC units | 52 |
| 8 ml (9.64) 20000 CMC units | 51 |
| Shaken control | 2 |

Conclusions:

(1) Maximum degradation was obtained with 4 ml enzyme (approx. 5%).

(2) Increasing the amount of enzyme did not increase the amount of degradation under these conditions.

(3) Compared to Rapidase® at 3 days, Indiage® degraded more cotton at the 4 and 8 ml concentrations (Rapidase®=40 and 44% respectively).

EXAMPLE 20

Same set up as Example 19.

Purpose:

To repeat Example 19 but extend the incubation period to 6 days

Results:

| Enzyme Concentration (mls & %) | % Cotton Degraded |
|---|---|
| 1 ml (1.33%) 2500 CMC units | 45 |
| 4 ml (5.06) 10000 CMC units | 67 |
| 8 ml (9.64) 20000 CMC units | 65 |
| Control | 4 |

Conclusions:

(1) Maximum degradation occurred at 4 and 8% concentrations of enzyme.

(2) Extending the incubation period to 6 days from 3 increased degradation at all concentrations of enzyme (but not in the control which lacked enzyme).

(3) Compared to Rapidase® at 6 days, Indiage® degraded at about the same cotton at the 4 and 8 ml concentrations (Rapidase®=63 and 62% respectively).

EXAMPLE 21

Indiage® (4 ml/75 ml medium) 10000 CMC units

50°–55° C. incubation temperature 200 rpm vary pH 6 day incubation period

Purpose:

To determine the effect of pH, and optimum pH, on cotton degradation in the presence of Indiage® enzyme. A control (minus enzyme) was run for each pH to ensure that degradation was not the result of pH alone.

Results:

| pH | +/− Enzyme | % Cotton Degraded |
|---|---|---|
| 4.0 | + | 28 |
| | − | 2 |
| 4.5 | + | 60 |
| | − | 2 |
| 5.0 | + | 77 |
| | − | 2 |
| 5.5 | + | 76 |
| | − | 3 |
| 6.0 | + | 59 |
| | − | 1 |

Conclusions:

(1) Maximum degradation under these conditions occurred at pH 5.0 and 5.5.

(2) Good degradation between pH 4.5 and 6.0; less at pH 4.0.

(3) No degradation in the absence of the enzyme, therefore, degradation not due to low pH.

EXAMPLE 22

Indiage® (4 ml) 10000 CMC units
pH 5.5 (buffered)
200 rpm
6 day incubation period
Purpose:
To determine the effect of temperature on cotton degradation.

Results:

| Temp | +/− Enzyme | % Cotton Degraded |
|---|---|---|
| 21–22 | + | 31 |
| | − | 3 |
| 40 | + | 20 |
| | − | 3 |
| 50 | + | 57 |
| | − | 0 |
| 55 | + | 3 |
| | − | 5 |
| 60 | + | 0 |
| | − | 0 |

Conclusions:

(1) Maximum degradation under these conditions occurred at 50° C.

(2) Enzyme inactive at 55° C.

(3) At room temperature and 40° C., less than half the amount of cotton was degraded as at 50° C.

(4) No degradation in "minus enzyme" controls at each temperature, thus temperature alone does not affect degradation.

(5) Observation: enzyme appears to have a narrower temp. range than Rapidase®.

Enzyme Experiments (Other than with Rapidase® or Indiage®)

Place 0.050 g of wool which has been dried to constant weight at 100 C in each of three test tubes (25×90 mm). Add 10 ml of McIlvaine buffer at the proper pH per tube and:

a) 2000 units of Protease, Type XIV, or b) Average of 10890 units of pepsin, or c) Average of 200 units of trypsin Control tubes without enzyme also are prepared. All tubes were incubated at the indicated temperature with agitation at 200 rpm for 48 hours. The residual wool was separated from the enzyme solution, dried to constant weight at 100° C. for 24 hours, and weighed.

EXAMPLE 23

Proteolytic enzymes:

protease at pH 7.5
Enzyme: Protease, Type XIV, Bacterial (Pronase E) (EC 3.4.24.4)
Manufacturer: Sigma Chemical Company
P.O. Box 14508
St. Louis, Mo. 63178-9916
Producing Organism: *Streptomyces griseus*
Activity: Approximately 4 units per mg solid powder trypsin at pH 7.6
Enzyme: Trypsin (EC 3.4.21.4)
From porcine pancreas
Activity: Average of 1250 units per mg solid
Manufacturer: Sigma Chemical Company
P.O. Box 14508
St. Louis, Mo. 63178-9916 pepsin at pH 2.0
Enzyme: Pepsin (Pepsin A; EC 3.4.23.1)
From porcine stomach mucosa
Activity: Average 1650 units per mg solid powder
Manufacturer: Sigma Chemical Company
P.O. Box 14508
St. Louis, Mo. 63178-9916
All enzyme solutions prepared in McIlvaine buffer
Raw wool
37° C. for protease and pepsin; 25° C. for trypsin
200 rpm
3 days
Purpose:
To determine if protein substrates such as raw wool and formed collagen can be degraded by proteolytic enzymes. Controls run without enzyme.

Results:

| Sorbent | Enzyme | % Sorbent Degraded |
|---|---|---|
| wool | protease | 14 |
| wool | pepsin | 0 |
| wool | trypsin | 0 |

Note: As part of this experiment, formed collagen pads soaked with diesel fuel or crude oil also were tested to see if they would degrade in the protease. This was a "quick" experiment; oil release was all that was determined. Ans.= yes in 3 days at 37° C. in the protease solution.

Conclusions:

(1) Wool can be degraded slightly in 3 days by the protease, but not by trypsin or pepsin.

(2) Collagen pads were degraded by the protease and released the oils in three days.

EXAMPLE 24

Proteases (Types IV, V, VI and XIV)

Enzyme: Protease, Type IV: Bacterial, purified (EC 3.4.24.4)

Manufacturer: Sigma Chemical Company
P.O. Box 14508

St. Louis, Mo. 63178-9916

Producing Organism: *Streptomyces capitosus*

Activity: 0.7–1.0 unit per mg solid

Enzyme: Protease, Type V (EC 3.4.24.4)

Manufacturer: Sigma Chemical Company
P.O. Box 14508
St. Louis, Mo. 63178-9916

Producing Organism: *Streptomyces griseus*

Activity: 0.7–1.0 unit per mg solid

Note: This item was discontinued by the manufacturer in 1980. It is the same enzyme as Type XIV, differing from it in that Type V contained a starch extender.

Enzyme: Protease, Type VI (EC 3.4.24.4)

Manufacturer: Sigma Chemical Company
P.O. Box 14508
St. Louis, Mo. 63178-9916

Producing Organism: *Streptomyces griseus*

Activity: 3–4 units per mg solid

Note: This item was discontinued by the manufacturer in 1980. It is the same enzyme as Type XIV, except it was referred to as Pronase P (P grade) rather than Pronase E.

Enzyme: Protease, Type XIV (EC 3.4.24.4)

Manufacturer: Sigma Chemical Company
P.O. Box 14508
St. Louis, Mo. 63178-9916

Producing Organism: *Streptomyces griseus*

Activity: Approximately 4 units per mg solid

Procedure:

0.5 g samples of dried raw wool were placed into Erlenmeyer flasks and 65 ml of McIlvaine buffer at pH 7.5 were added. Four different types of proteases, Type IV, V, VI and XIV were added at various activities as indicated. All flasks were incubated on a shaker at 200 rpm for 6 days at 37° C. The residual wool was recovered by filtration, dried and weighed.

pH 7.5 buffered

37° C. incubation temperature 200 rpm 6 days

Purpose:

To determine if other proteases can degrade wool.

Results:

| Sorbent | Enzyme | % Sorbent Degraded |
|---|---|---|
| wool | protease IV 65 units | 27 |
| wool | protease V 65 units | 18 |
| wool | protease VI 260 units | 20 |
| wool | protease XIV 260 units | 16 |

Conclusions:

(1) All were about as effective as the protease used in Example 23.

(2) A little more degradation after 6 days as compared to Example 23 (3 days).

Papain (EC 3.4.22.2)

Source: papaya latex

Manufacturer: Spectrum Chemical Manufacturing Co.
14422 S. San Pedro St.
Gardenia, Calif. 90248-9985
(310) 516-8000

Activity: 200 milk clotting units per gram (the manufacturer's definition of a milk clotting unit is as follows:

"The milk clot assay is based on the proteolytic hydrolysis of a buffered milk substrate at 40° C. Enzyme activity is related to the time required to clot 25 ml of substrate.")

Sodium bisulfite, granular reagent, ACS

Manufacturer: Spectrum Chemical Manufacturing Co.
14422 S. San Pedro St.
Gardenia, Calif. 90248-9985

Procedure:

The procedure in Example 25 was the same as Example 24 except that: a) the enzyme tested was papain, 0.05 milk clotting units per ml, in the presence of sodium bisulfite (2.0%) at pH 6.5–7.5 with a total volume of 75 ml, b) the incubation temperature was 65° C. and c) the incubation period varied as noted in the example.

EXAMPLE 25

Papain (0.025%) with sodium bisulfite (2.0%) 0.05 milk clotting units/ml pH 6.5–7.5 (buffered)

65° C. incubation 200 rpm 1, 3, 6, 9, 12 days incubation raw wool

Purpose:

To determine if papain in the presence of sodium bisulfite degrades raw wool better than the proteases.

Results:

| Days incubation | % Wool Degraded |
|---|---|
| 1 | 93 |
| 3 | 90 |
| 6 | Dried |
| 9 | Dried |
| 12 | Dried |

3 controls without enzyme but with sodium bisulfite = 10% degradation

Conclusions:

(1) Papain and sodium bisulfite successfully degraded wool.

Further Cotton Examples 0.5 gram samples of raw cotton which had been dried and weighed to ±0.1 mg were placed in individual Erlenmeyer flasks with 75 ml of McIlvaine buffer at pH 7.0 plus (4 ml DenimaxL® solution) 360 EGU DenimaxL®, another commercial cellulase. Incubation on a shaker at 200 rpm was carried out for 6 days at various temperatures, as indicated. The cotton residue then was recovered, dried and weighed to calculate per cent fiber digested. (Assumed that 1 ml of DenimaxL® solution equal to one gram; thus contained 90 EGU.)

EXAMPLE 26

Denimax cellulase 360 EGU pH 7 (pH 6–8 mfg. recommended)

various temperatures (room temp., 45°, 50°, 55° and 60° C. - mfg. recommends 50°–60° C.)

200 rpm 6 days

Purpose:

To determine if another type of cellulase (Denimax) which runs at a higher pH can degrade raw cotton; if so, how much.

Results:

| Temp | +/– Enzyme | % Cotton Degraded |
|---|---|---|
| room | + | 10 |
|  | – | 7 |
| 45 | + | 16 |
|  | – | 16 |
| 50 | + | 19 |
|  | – | 14 |
| 55 | + | 3 |
|  | – | 8 |
| 60 | + | 7 |
|  | – | 7 |

Conclusions:

(1) Under these conditions; this enzyme did not work well.

The procedure for Example 27 was the same as that for Example 26, with 3000 EGU Cellusoft®, another commercial cellulase, replacing the Denimax® enzyme. (Same assumption—one ml equal one gram.)

EXAMPLE 27

Cellusoft® cellulase 3000 EGU pH 7 (pH 4.5–5.5 mfg. recommended)

various temperatures (room temp., 45°, 50°, 55° and 60° C. - mfg. recommends 45°–55° C.)

Purpose:

To determine if another type of cellulase (Cellusoft®) which runs at a higher pH can degrade raw cotton; if so, how much.

Results:

| Temp | +/– Enzyme | % Cotton Degraded |
|---|---|---|
| room | + | 0 |
|  | – | 2 |
| 45 | + | 20 |
|  | – | 4 |
| 50 | + | 0 |
|  | – | 1 |
| 55 | + | 0 |
|  | – | 1 |
| 60 | + | 0 |
|  | – | 1 |

Conclusions:

(1) Used wrong pH; mfg. recommended 4.5–5.5.

(2) Even under these conditions, got better degradation than the (minus enzyme) controls at 45° C.

(3) Experimental=controls at other temperatures.

The procedure for Example 28 was the same as that for Examples 6–9 except that agitation speed (rpm) was varied as indicated to determine the effect of this variable.

EXAMPLE 28

Rapidase® (4 ml) 408 CCU pH 4.5

40° C.

6 days incubation

Purpose:

To determine if increasing agitation speed increases the amount of cotton degraded by Rapidase® in 6 days. A static control (no agitation, listed below as "0" rpm) was included.

Results:

| RPM | +/– Enzyme | % Cotton Degraded |
|---|---|---|
| 0 | – | 4 |
| 0 | + | 38 |
| 50 | – | 2 |
| 50 | + | 39 |
| 100 | – | 3 |
| 100 | + | 53 |
| 200 | – | 1 |
| 200 | + | 60 |
| 250 | – | 1 |
| 250 | + | 64 |
| 300 | – | 0 |
| 300 | + | 63 |
| 350 | – | 0 |
| 350 | + | 67 |
| 400 | – | 0 |
| 400 | + | 66 |

Conclusions:

(1) No degradation in the absence of enzyme.

(2) No agitation (0 rpm) after 6 days led to measurable degradation (38%).

(3) 50 rpm was not better than no agitation (0 rpm).

(4) 100 to 400 rpm led to considerably more cotton degradation than 0 or 50 rpm.

(5) Slightly better cotton degradation at 200–400 rpm than at 100 rpm.

(6) No appreciable difference regarding the amount of cotton degraded between 200 and 400 rpm.

Example 28 agitation studies were conducted on a Lab Line Gyrotary (shaker) utilizing 125 ml flask amounted on a platform, rpm refers to platform rotation.

EXAMPLE 29

Degradation of crude soaked wool by Papain

Purpose:

To determine if wool soaked with crude oil can be degraded with papain in the 2% sodium bisulfite solution (with the pH adjusted to 6.85 with soda ash), thereby releasing the crude oil which then floats to the top of the solution.

Procedure:

0.50 gram samples of raw wool were dried at 100° C. and samples weighed to ±1 mg. Individual wool samples were placed in 75 ml of a 2% solution of sodium bisulfite (pH adjusted to 6.85 with soda ash) which contained 3.75 milk-clotting units of papain (=0.05/ml), and incubated at 65° C. on a gyrotary shaker at 200 rpm for 6 days. Distilled water was added to flasks as needed to maintain the initial volume because of evaporation which occurred at 65° C. At the end of the incubation period, the residual fiber was recovered, dried and weighed.

Design:

Media: 2% solution of sodium bisulfite @ pH 6.85 (75 ml/flask)

Sorbent: 0.5 grams of raw wool (New Zealand #6)

Enzyme: Papain 0.05 milk clotting units per ml

Time: Six days

Temp: 65° C.

Agitation: 200 rpm

Treatments: in triplicate 3 control (raw wool without oil)

3 raw wool with crude

Total=6 flasks

The experiment was started on day 1 and by day 2 there was no visible structure left in the controls, and the group treated with crude oil had released the crude. However, for the samples treated with crude, degradation was not as complete as the controls, so there were still some short fibers interspersed in the crude layer at the end of the experiment. As a result, removal of the crude layer with a vacuum was not done and instead, as much of the crude as possible was washed off the fibers with hexane. Because this method was used, the post weights for the crude group will likely be higher than they should. Finally, since the temperature is relatively high, there was evaporation of the media and the starting volume had to be restored by the addition of distilled water during the incubation period.

Results:

| Sample | Mean % Wool degraded, n = 3 |
|---|---|
| Wool control (no crude oil) | 55 |
| Wool saturated with crude oil | 14 |

Conclusions:

Oil was released from the crude oil-soaked wool samples; release was not complete as a few wool fibers were mixed with the crude oil.

EXAMPLE 30

Purpose:

This experiment was performed to determine if wool and wool soaked with crude oil could be degraded by a solution of papain and sodium bisulfite in the presence of artificial seawater (Instant Ocean®).
Design:
Media: 2% solution of sodium bisulfite with 0.03% Instant Ocean® salts (4.5 g per 500 ml) added @ pH 6.85 (75 ml/flask)
Sorbent: 0.5 grams of raw wool from the Textile Research Center
Enzyme: Papain 0.10 milk clotting units per ml
Time: Six days
Temp: 65° C.
Agitation: 200 rpm
Treatments: in triplicate
3 control (raw wool without oil)
3 raw wool with crude
Total=6 flasks The experiment was started on day 1 and by day 2 the group treated with crude oil had released the crude. The initial volume was restored by adding distilled water on day 3. By day 4 almost total degradation in the control group was observed. Volume was restored once again on day 5 by addition of distilled water. Extensive degradation in both groups was observed.

Results:

| Sample | Mean % Wool degraded, n = 3 |
|---|---|
| Wool | 60 |
| Wool + Crude | 74 |

Conclusions:

Under the conditions tested, papain degraded raw wool soaked with crude oil in the presence of seawater.

EXAMPLE 31

Papain 0.05 milk clotting units/ml
Sodium bisulfite (2% solution), pH 6.85
Total volume=75 ml per flask
Raw wool, 0.5 g
Treatments:
 3 control raw wool without oil 3 raw wool with crude oil (W. Texas light crude)
 65° C.
 200 rpm
 6 day incubation period
Purpose:

To determine whether crude oil can be released from raw wool using a 2% solution of sodium bisulfite containing the enzyme papain.
Results:

Degradation of the wool, as determined by the disappearance of the fibers occurred in all flasks. Crude oil was released from the wool in the three flasks containing the oil-soaked wool. The amount of residual wool was determined after drying the material recovered by filtration of the enzyme solution after removal of the oil.

| Percent Degradation | |
|---|---|
| Control (no oil) | + Crude Oil |
| 52.68 | 19.39 |
| 56.32 | 11.56 |
| 63.47 | 10.40 |
| Mean +/− SE: | |
| 57.49 +/− 3.17 | 13.78 +/− 2.83 |

Conclusions:

Under the conditions tested, papain degraded raw wool and released the entrained crude oil.

Examples 1–31 illustrate various refinements in accordance with the invention as compared to comparative examples which are outside the invention. Unexpected results were achieved in view of the prior art teachings, in Example 1, no statistical difference in the amount of degradation between raw cotton and a processed or a commercially available cotton pad was observed. Maximum degradation of cotton utilizing cellulase was found to occur in concentrations of the enzyme of between about 4 and 8% by volume of the reaction aqueous medium. Example 4 illustrates pH controls wherein good degradation was achieved between a pH of 3.5 and about 6.0 with less satisfactory results at a pH of 7.0. Cellulase degradation of cotton is found to provide maximum degradation in the aqueous solution at conditions of 40° C. with good degradation also at 50° and 55° C. Apparently enzyme activity ceases at temperatures of about 65° C. Diesel or crude oil adsorbed on cotton within the inventive aqueous medium utilizing cellulase was released and floats to the top of the container as the result of cotton degradation by the enzyme, as seen in the results of Example 10.

Example 11 utilizing various concentrations of enzymes provided time studies wherein the degradation of the cotton fibers was sufficient to allow the adsorbed oil to be released and recovered from the surface of the aqueous medium. Such timing occurred between about 2 hours and 24 hours. Under ideal conditions such as enzyme concentration, temperature of the aqueous medium and selection of enzymes, petroleum product release from the cotton fibers has been observed to occur at about 2 hours.

The process according to the invention was found to be of useful when the aqueous medium is comprised of seawater. In Example 28 impact of the additional enhancement variable, agitation of the aqueous medium containing the enzyme and the natural fiber which contains adsorbed petroleum products is shown. The enzymes utilized showed considerable tolerance to agitation, however enzyme activity may be impacted adversely by exaggerated shear forces.

Examples 29–31 illustrate that papain is able to degrade raw wool soaked with crude oil both in the presence and absence of Instant Ocean® salts (simulated seawater). In this regard, the papain-wool system is similar to the Rapidase®-cotton system since both enzyme preparations are capable of degrading the appropriate natural organic fibers when soaked with crude oil, both in the presence and absence of simulated seawater.

Several examples address the concept of reusing cellulase enzyme solutions after said solutions were separated from the aqueous reaction medium on a continuous recycle methodology. Approximately 10% loss in activity was observed versus new enzyme solutions.

Cotton was degraded by the commercial enzyme, Indiage®, as compared to the commercial enzyme for cotton degradation Rapidase®. Both commercial preparations performed in accordance with the invention with similar results. Comparison of the various enzyme preparations, i.e. commercial preparations, indicate slight variations in pH, temperature and concentration refinements.

In the degradation of wool the enzyme protease is found to perform at a low concentration level for satisfactory degradation of the fiber. In Example 25 the enzyme papain in the presence of a reducing agent, sodium bisulfite, degrades wool at a very high level, for example, after one day of incubation, 93% wool degradation. Example 29 shows that papain in the presence of sodium bisulfite degrades wool soaked with crude oil, releasing the oil. Example 30 shows that oil release from wool can be accomplished in seawater using papain and sodium bisulfite. Example 31 is similar to Example 29, but shows the amount of wool which was degraded. Other methods of preparing wool fibers for enzyme degradation include mechanical milling and the like or the chemical reduction of wool fibers either before or simultaneously with the enzyme degradation processes.

While various embodiments of the invention have been described using specific terms, and examples, such description is for illustrative purposes only, and it is to be understood that changes and variations may be made without departing from the spirit and scope of the following claims.

What is claimed is:

1. A method for separating crude oil petroleum products or other non-aqueous organic liquids adsorbed on organic natural fibers through enzyme degradation reduction of the fibers length and size, comprising:

admixing in a reaction chamber organic natural fibers selected from the group consisting of cellulosic and protein-based fibers containing adsorbed petroleum products with an effective amount of enzymes to degrade the organic natural fibers sufficiently to release the trapped oil in an aqueous medium, said enzymes capable of degrading the fibers;

maintaining the admixture at a pH of from about 3.5 to about 8.0 and a temperature of from about 20° C. to about 65° C., as is sufficient to maintain the enzymes active;

degrading the organic natural fibers by enzyme breakage of the molecular chains constituting the fibers;

destroying the integrity of the organic natural fiber, by about 28% or greater sufficient for release of the adsorbed petroleum products;

removing the released petroleum products from the aqueous medium surface; and disposing of the aqueous medium, degraded fibers and resulting byproducts.

2. The method according to claim 1 for separating petroleum products adsorbed on organic natural fibers wherein the aqueous medium admixture of organic natural fibers containing adsorbed petroleum products and enzymes are agitated for enhancing the degradation process.

3. The method according to claim 1 for separating petroleum products adsorbed on organic natural fibers wherein the aqueous medium containing adsorbed petroleum products and enzymes are removed from the reaction chamber with the enzyme solution being recovered and reused for additive degradation of organic natural fibers containing adsorbed petroleum products, the reused enzymes being supported by up to about 10% by volume of fresh enzyme solution containing the same activity as the original solution introduction to the reaction mixture.

4. The method according to claim 1 wherein the adsorbed petroleum products are released in about 2 to 3 hours and the oil released accumulates on the surface of the aqueous medium for removal.

5. The method for separating petroleum products adsorbed on natural fibers according to claim 1 wherein the enzyme concentration in the aqueous medium containing said fibers and petroleum products is from about 4% to about 30% O. W. G.

6. The method for separating petroleum products adsorbed on natural fibers according to claim 1 wherein at the removal of released petroleum products, the viscosity and density is reduced by dilution with kerosene or other lighter hydrocarbons.

7. The method for separating petroleum products adsorbed on organic natural fibers according to claim 1 wherein the natural fibers are comprised of cellulose or modified cellulose materials and the enzymes are comprised of cellulases.

8. The method for separating petroleum products adsorbed on organic natural fibers according to claim 7 wherein the cellulose or modified cellulose materials can contain up to about 40% by weight of man-made fibers or other natural fibers.

9. The method according to claim 1 wherein removing the released oil from the aqueous medium surface is accomplished by skimming.

10. The method according to claim 1 for separating petroleum products adsorbed on protein fibers wherein the aqueous medium admixture of protein fibers containing adsorbed petroleum products and enzymes are agitated for enhancing the degradation process.

11. A method for separating petroleum product absorbed on cellulosic fibers through enzyme degradation reduction of the cellulosic fibers length and size, comprising:

admixing in a reaction chamber the cellulosic fibers containing absorbed petroleum products with cellulases in sufficient concentration to degrade the cellulosic fibers in an aqueous medium;

maintaining the mixture at a pH of from about 4 to about 6.5 at a temperature of from about 20° C. to about 65° C., as is sufficient to maintain the cellulases active;

agitating the aqueous medium containing the cellulases and cellulosic fibers containing absorbed petroleum products;

degrading the cellulosic fibers by breakage of the cellulose molecule chains;

reducing the cellulose chain links by destroying the $\beta$ 1–4 glycosidic bonds of cellulose thus reducing the length of the cellulosic fibers by about 28% or greater and releasing the absorbed petroleum products;

removing the released petroleum products from the aqueous medium surface; and disposing of the environmentally acceptable aqueous medium, degraded fibers and resulting byproducts in an environmentally acceptable manner.

12. The method for separating petroleum products adsorbed on cellulosic fibers according to claim 11 wherein the admixture of aqueous medium, cellulases and cellulosic fibers containing adsorbed petroleum products are removed from the reaction chamber with the cellulases being reused for additional degradation of fibers, the reused cellulases being made-up by up to about 10% by volume of fresh cellulase solution containing the same activity as the original solution introduction to the reaction mixture.

13. The method according to claim 11 wherein the petroleum products are released in about 2 hours and accumulate on the surface of the aqueous medium forming a separate petroleum products layer which is removed from the aqueous medium mixture.

14. The method for separating petroleum products adsorbed on cellulosic fibers according to claim 11 wherein the cellulase concentration in the aqueous medium containing said fibers in petroleum products is from about 100 activity units per ml per 0.5 gram of fiber to about 2500 activity units per ml per 0.5 gram of fiber.

15. The method for separating petroleum products adsorbed on cellulosic fibers according to claim 11 wherein the cellulosic fibers contain up to about 40% by weight of man-made fibers or other natural fibers.

16. The method for separating petroleum products adsorbed onto natural fibers according to claim 11 wherein after removing the released petroleum products from the aqueous medium surface the viscosity and density are adjusted by dilution with kerosene or other lighter hydrocarbon added to the admixture.

17. The method according to claim 11 wherein removing the released oil from the aqueous medium surface is accomplished by skimming.

18. The method according to claim 11 for separating petroleum products adsorbed on cellulosic fibers wherein the aqueous medium admixture of cellulosic fibers containing adsorbed petroleum products and enzymes are agitated for enhancing the degradation process.

19. A method of removing oil from the surface of water comprising:

contacting the oil with organic natural fibers;

adsorbing the oil onto the organic natural fibers selected from the group consisting of cellulosic and protein-based fibers;

removing the organic natural fibers having adsorbed petroleum products content from the water surface;

admixing in a reaction chamber the organic natural fibers containing adsorbed petroleum products with enzymes capable of degrading the fibers in an aqueous medium;

maintaining the mixture at a pH of from about 3.5 to about 7.0 at a temperature of from about 20° C. to about 60° C., as is sufficient to maintain the enzymes active;

degrading the organic natural fibers by enzyme breakage of the molecular chains constituting the fibers;

reducing the links of the chains and lengths of the fibers by about 28% or greater, sufficient for release of adsorbed petroleum products;

removing the released petroleum products from the aqueous medium surface; and disposing of the environmentally acceptable aqueous medium, degraded fibers and resulting byproducts.

20. The method according to claim 19 for separating petroleum products adsorbed on organic natural fibers wherein the aqueous medium admixture of organic natural fibers containing adsorbed petroleum products and enzymes are agitated for enhancing the degradation process.

21. The method according to claim 19 for separating petroleum products adsorbed on organic natural fibers wherein the aqueous medium containing adsorbed petroleum products and enzymes are removed from a reaction chamber with the enzymes being reused for additive degradation of organic natural fibers containing adsorbed petroleum products, the reused enzymes being made-up by up to about 10% by volume of fresh enzyme solution containing the same activity as the original solution introduction to the reaction mixture.

22. The method according to claim 19 wherein removing the released oil from the aqueous medium surface is accomplished by skimming.

23. The method for separating petroleum products adsorbed on organic natural fibers according to claim 19 wherein the enzyme concentration in the aqueous medium containing said fibers and petroleum products is from about 1 activity unit per ml per 0.5 gram of fiber to about 250 activity units per ml per 0.5 gram of fiber.

24. The method for separating petroleum products adsorbed on organic natural fibers according to claim 19 wherein at the removal of released petroleum products, the viscosity and density is reduced by dilution with kerosene or other lighter hydrocarbons.

25. The method for separating petroleum products adsorbed on organic natural fibers according to claim 19 wherein the organic natural fibers are comprised of cellulose or modified cellulose materials and the enzymes are comprised of cellulases.

26. The method for separating petroleum products adsorbed on organic natural fibers according to claim 25 wherein the cellulose or modified cellulose materials contain up to about 40% by weight of man-made fibers or other natural fibers.

27. The method according to claim 19 for separating petroleum products adsorbed on protein fibers wherein the aqueous medium admixture of protein fibers containing adsorbed petroleum products and enzymes are agitated for enhancing the degradation process.

28. A method for separating petroleum products adsorbed on protein fibers through enzyme degradation reduction of the protein fibers length and size, comprising:

admixing in a reaction chamber said protein fibers containing adsorbed petroleum products with a protease with 0.05 activity units per ml per 0.5 gram fiber to 260 activity units per ml per 0.5 gram fiber and greater to degrade the protein fibers;

maintaining the admixture at a pH of from about 6.0 to 8.0 and at a temperature of from about 20° C. to about 65° C., as is sufficient to maintain the protease active;

degrading the protein fibers by enzyme breakage of the molecular chains constituting the protein fibers;

destroying the integrity of the natural fiber, fiber lengths by about 28% or greater, sufficient for release of the adsorbed petroleum products;

removing the released petroleum products from the aqueous medium surface; and disposing of the aqueous medium, degraded protein fibers and resulting byproducts.

29. The method according to claim 28 wherein said the protein fibers are comprised of wool and are treated by reducing agents.

30. The method according to claim 29 wherein the reducing agent is sodium bisulfite and is added to the aqueous reaction medium along with the protease and wool fibers containing adsorbed petroleum products.

31. The method according to claim 29 for separating petroleum products adsorbed on protein fibers wherein the aqueous medium admixture of protein fibers containing adsorbed petroleum products and protease are agitated for enhancing the degradation process.

32. The method according to claim 28 for separating petroleum products adsorbed on protein fibers wherein the aqueous medium containing adsorbed petroleum products and enzymes are removed from a reaction chamber with the enzymes being reused for additive degradation of natural fibers containing adsorbed petroleum products, the reused enzymes being made-up by up to about 10% by volume of fresh enzyme solution containing the same activity as the original solution introduction to the reaction mixture.

33. The method according to claim 28 wherein the released oil from the aqueous medium surface is accomplished by skimming.

34. The method for separating petroleum products adsorbed on protein fibers according to claim 28 wherein the enzyme concentration in the aqueous medium containing said fibers and petroleum products is from about 0.05 activity units per ml per 0.5 gram fiber to 260 activity units per ml per 0.5 gram fiber and greater.

35. An aqueous medium composition of organic natural fibers, adsorbed petroleum products on said natural fibers and enzymes capable of degrading said fibers for separation of the petroleum products from said organic fibers comprising:

the enzymes constituting of from about 0.05 activity units per ml per 0.5 gram fiber to about 260 activity units per ml per 0.5 gram fiber and greater and the reaction mixture having a pH of from about 3.5 to about 8.0 and a temperature of from about 20° C. to about 65° C.

36. An aqueous medium composition of cellulosic fibers, adsorbed petroleum products on said cellulosic fibers and cellulase, said composition suitable for separation of the petroleum products from the cellulosic fibers comprising:

the cellulase constituting of from about 100 activity units/ml/0.5 g fiber to about 2500 activity units/ml/0.5 g fiber; and the reaction mixture having a pH of from about 3.5 to 6.5 and a temperature of from about 20° C. to about 60° C.

37. An aqueous medium composition of protein fibers, adsorbed petroleum products on said protein fibers and enzymes capable of degrading said protein fibers as well as a reducing agent, the combination of the enzymes and reducing agents capable of degrading the protein fibers for separation of the petroleum products from said protein fibers comprising:

the enzymes constituting of from about 0.05 activity units/ml/0.5 gram to about 260 activity units/ml/0.5 gram and greater; and the reaction mixture having a pH of from about 6 to 8 and a temperature of from about 20° C. to about 65° C.

38. An aqueous medium composition according to claim 37 wherein the protein fibers are comprised of wool fibers and the enzyme is protease.

39. An aqueous medium composition according to claim 37 wherein the aqueous medium is seawater.

* * * * *